(12) United States Patent
Chen et al.

(10) Patent No.: US 10,354,857 B2
(45) Date of Patent: Jul. 16, 2019

(54) HIGH POWER LOW PRESSURE UV BULB WITH PLASMA RESISTANT COATING

(71) Applicant: LAM RESEARCH CORPORATION, Fremont, CA (US)

(72) Inventors: Xiaolan Chen, Tigard, OR (US);
Matthew Mudrow, Tigard, OR (US);
Curtis Bailey, West Linn, OR (US);
Stephen Lau, Lake Oswego, OR (US);
Mitchell Lamar, Vancouver, WA (US)

(73) Assignee: LAM RESEARCH CORPORATION, Fremont, CA (US)

( * ) Notice: Subject to any disclaimer, the term of this patent is extended or adjusted under 35 U.S.C. 154(b) by 59 days.

(21) Appl. No.: 15/389,930

(22) Filed: Dec. 23, 2016

(65) Prior Publication Data

US 2018/0182607 A1 Jun. 28, 2018

(51) Int. Cl.
*H01J 61/35* (2006.01)
*H01J 65/04* (2006.01)
(Continued)

(52) U.S. Cl.
CPC ............ *H01J 61/35* (2013.01); *H01J 61/12* (2013.01); *H01J 61/322* (2013.01);
(Continued)

(58) Field of Classification Search
None
See application file for complete search history.

(56) References Cited

U.S. PATENT DOCUMENTS

| | | |
|---|---|---|
| 7,208,389 B1 | 4/2007 | Tipton et al. |
| 7,569,791 B2 | 8/2009 | Smith et al. |

(Continued)

FOREIGN PATENT DOCUMENTS

WO 2013115919 A1 8/2013

OTHER PUBLICATIONS

International Search Report and Written Opinion dated Mar. 30, 2018 in corresponding International Patent Application No. PCT/US2017/065804, 14 pages.

(Continued)

*Primary Examiner* — Alexander G Ghyka
(74) *Attorney, Agent, or Firm* — Buchanan Ingersoll & Rooney PC

(57) ABSTRACT

An envelope of an ultraviolet (UV) bulb comprises a tube of UV transmissive material configured to contain a UV emissive material and a plasma resistant coating on an inner surface of the tube wherein the coating has been deposited by atomic layer deposition (ALD) and is the only material attached to the inner surface of the tube. The tube can be an endless tube having a circular shape and the coating can be an ALD aluminum oxide coating. The UV transmissive material can comprise quartz or fused silica and the tube can have a wall thickness of about 1 to about 2 mm. The coating can have a thickness of no greater than about 200 nm such as about 120 nm to 160 nm. The circular tube can be formed into a torus shape which can have an outer diameter of about 200 mm and the tube itself can have an outer diameter of about 30 mm. The ALD aluminum oxide coating can be a pinhole free conformal coating. A UV bulb comprising the envelope can contain mercury and inert gas such as argon with pressure inside the UV bulb below 100 Torr. A method of curing a film on a semiconductor substrate, comprises supporting a semiconductor substrate in a curing chamber and exposing a layer on the semiconductor substrate to UV radiation produced by the UV bulb. Other uses include semiconductor substrate surface cleaning or sterilization of fluids and objects.

18 Claims, 6 Drawing Sheets

46nm coating (1072hr)

(51) Int. Cl.
*H01L 21/26* (2006.01)
*H01J 61/12* (2006.01)
*H01J 61/32* (2006.01)
*A61L 2/10* (2006.01)
*A61L 9/20* (2006.01)

(52) U.S. Cl.
CPC ............ *H01J 65/042* (2013.01); *H01L 21/26* (2013.01); *A61L 2/10* (2013.01); *A61L 9/20* (2013.01); *A61L 2202/11* (2013.01); *A61L 2209/212* (2013.01)

(56) References Cited

U.S. PATENT DOCUMENTS

| | | | |
|---|---|---|---|
| 8,137,465 | B1 | 3/2012 | Shrinivasan et al. |
| 9,073,100 | B2 | 7/2015 | Gytri et al. |
| 9,142,397 | B2 | 9/2015 | Du et al. |
| 9,269,559 | B1 | 2/2016 | Jansma et al. |
| 2003/0071571 | A1 | 4/2003 | Yu et al. |
| 2005/0109463 | A1 | 5/2005 | Sellars |
| 2006/0165904 | A1 | 7/2006 | Ohara |
| 2008/0213129 | A1 | 9/2008 | Van der Pol et al. |
| 2013/0177706 | A1* | 7/2013 | Baluja .................. B05D 3/066 427/226 |
| 2013/0193835 | A1 | 8/2013 | Cohen et al. |
| 2015/0368822 | A1 | 12/2015 | Sammelselg et al. |
| 2016/0138160 | A1 | 5/2016 | Lambert et al. |
| 2016/0258057 | A1 | 9/2016 | Lee et al. |

OTHER PUBLICATIONS

A.V Levchenko et al., "Protective coating with a mixed composition for low-pressure discharge Amalgam lamps", Surface Engineering and Applied Electrochemistry, 2015, vol. 51, No. 1, pp. 54-57.

A. I. Vasil et al., "Investigation of the effect of a protective layer on parameters of quartz low-pressure gas-discharge lamps with oxide electrodes", Surface Engineering and Applied Electrochemistry, 2007, vol. 43 No. 1 pp. 49-52.

A.V Krasnochub et al., "Qualitative model of the operating mechanism of the protective coating for low pressure Hg lamps", J. of Phys. D: Appl. Phys. 39(2006) 1378-1383.

D A Doughty et al., "Mercury-glass interactions in Fluorescent lamps", J. Electrochem, Soc., vol. 142, No. 10 Oct. 1995, p. 3542-3550.

B J Mulder et al., "Mechanism of Glass darkening by a low pressure mercury discharge", J. Electrochem, Soc., Feb. 1983, p. 440-449.

G. Dingemans et al., "Status and prospects of Al2O3-based surface passivation schemes for silicon solar cells,", J. Vac. Sci. Technology, 2012 American Vacuum Society, vol. 30, No. 4, Jul./Aug. 2012, p. 040802-1 to 040802-27.

* cited by examiner

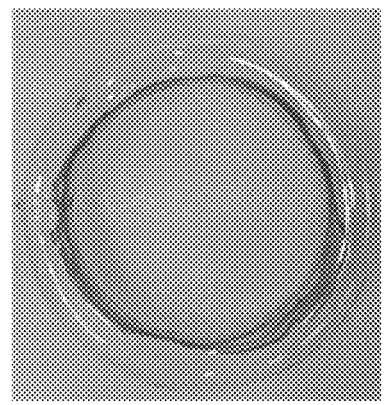
FIG. 4A No coating (94hr)
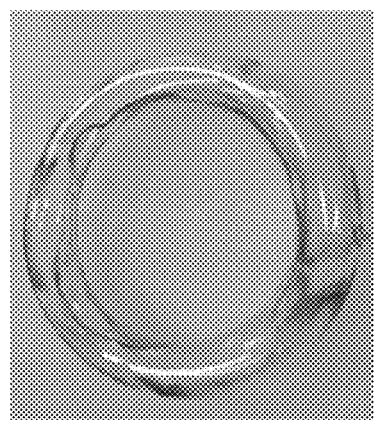
FIG. 4B 46nm coating (1072hr)
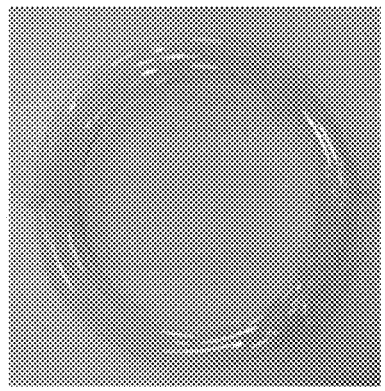
FIG. 4C 140nm coating (2416hr)

HIGH POWER LOW PRESSURE UV BULB WITH PLASMA RESISTANT COATING

BACKGROUND

The invention relates to improvements in ultraviolet lamps useful for processing semiconductor substrates and other uses.

For ultraviolet (UV) curing, especially for semiconductor related applications, high deep UV and sub-200 nm radiations are desired. Although there are high power, high pressure Hg bulbs available for UV curing, the high Hg pressure (typically >1000 Torr) provides insufficient emissions below 200 nm. Low pressure Hg and amalgam bulbs have efficient emissions at 254 nm and 185 nm, but the power is too low to be used for applications demanding high deep UV output.

It has been discovered that high power, low pressure (<100 Torr) UV lamps of the type disclosed in U.S. Pat. No. 7,569,791 have short bulb lifetime (typically <100 hours) which makes such UV lamps uneconomical for semiconductor related or other applications. Thus, there is a need for improving bulb's lifetime of high power, low pressure UV lamps for semiconductor related applications or other applications.

SUMMARY

In accordance with one embodiment, an envelope of an ultraviolet bulb is provided which can be used in processing of semiconductor substrates or other applications such as curing of adhesives, inks, coatings; sterilization of fluids and objects. The envelope comprises a glass tube configured to contain an emissive material and a plasma resistant coating on an inner surface of the glass tube wherein the coating has been deposited by atomic layer deposition (ALD).

In accordance with various preferred embodiments, the envelope comprises a tube of UV transmissive material configured to contain a UV emissive material and the plasma resistant coating is the only material attached to the inner surface of the tube; the tube is an endless tube preferably having a circular shape; the coating is an ALD aluminum oxide coating; the UV transmissive material comprises quartz or fused silica; the tube has a wall thickness of about 1 to about 2 mm; the coating has a thickness of about 100 to about 200 nm, preferably about 120 to about 160 nm; when used for processing semiconductor wafers having a diameter of at least 200 mm, the tube can be formed into a torus shape which has an outer diameter of about 200 mm and the tube itself can have an outer diameter of about 30 mm; and/or the ALD aluminum oxide coating is preferably a pinhole free and conformal coating.

In an embodiment, a UV bulb comprises the envelope and the envelope contains a UV emissive material; the UV emissive material comprises mercury; the tube is hermetically sealed and includes an inert gas such as argon; pressure inside the bulb is below 100 Torr; when used for processing semiconductor wafers having a diameter of at least 200 mm, the tube can be an endless tube having a torus shape with an outer diameter of about 200 mm; and/or the coating is an ALD coating which is preferably a pinhole free and conformal coating.

According to a further embodiment, a UV lamp assembly includes the UV bulb and the UV lamp assembly can be used for processing a semiconductor substrate by exposing the semiconductor substrate to UV radiation produced by the UV bulb.

In an embodiment, a method of processing a semiconductor substrate comprises supporting a semiconductor substrate in a processing chamber and exposing the semiconductor substrate to UV radiation produced by the UV bulb. For example, the semiconductor substrate can include one or more dielectric layers and the UV radiation can be used to remove porogens from the one or more dielectric layers, increase strength of the one or more dielectric layers and/or repair damage to the one or more dielectric layers. In another method, a semiconductor substrate is supported in a processing chamber, ozone is generated by exposing an oxygen containing gas to UV radiation produced by the UV bulb, and the semiconductor substrate surface is cleaned with the ozone.

In a further embodiment, the UV bulb can be used for sterilizing a fluid or object. For example, the method can include energizing the UV bulb and exposing UV radiation produced by the UV bulb to a fluid or object for a duration of time sufficient to provide effective sterilization of microorganisms within the fluid or effective sterilization of microorganisms on a surface of the object.

BRIEF DESCRIPTION OF THE DRAWINGS

FIGS. 4A-C show the status of three UV bulbs as a function of time under the same high power (14~15 W/cm$^2$) conditions.

DETAILED DESCRIPTION

UV treatment of semiconductor wafers has many applications including removing porogens, strengthening dielectric films, repairing damage to low k films, stabilizing FSG films, improving hermeticity and selectivity of SiC etch stop films, curing nitrides and oxides, extracting water produced in dielectric (e.g., silicon oxide) deposition, densification of dielectric materials, and increasing stress in dielectric films (for, e.g., strained gates). UV curing has also been employed to lower the k-value of other dielectric materials such as oxides deposited by pulse deposition layer (PDL) processes.

For example, as device geometry shrinks, integrated circuits (IC) require dielectric films with smaller capacitance values. IC manufacturers have obtained low capacitance by inducing porosity in these dielectric films. Inclusion of porosity in dielectric films is accomplished by co-depositing the backbone dielectric material (typically an organo-silicate glass or OSG) with a pore generator (typically an organic material). However, inducing this kind of porosity causes degradation in the mechanical properties of the film, reducing its ability to sustain subsequent integration steps without mechanical damage. After the deposition, the pore generator (porogen) must be removed from the ULK precursor film, and the backbone dielectric material strengthened for further processing. UV radiation can be used to achieve both the porogen removal and the strengthening of the backbone dielectric material. The UV radiation drives out the porogen from the dielectric film and rearranges the bond structure in the residual material to strengthen it and to render it capable of sustaining subsequent processing. The cured film may have an ultra-low dielectric constant (k) of about 2-2.5.

Figure 1:
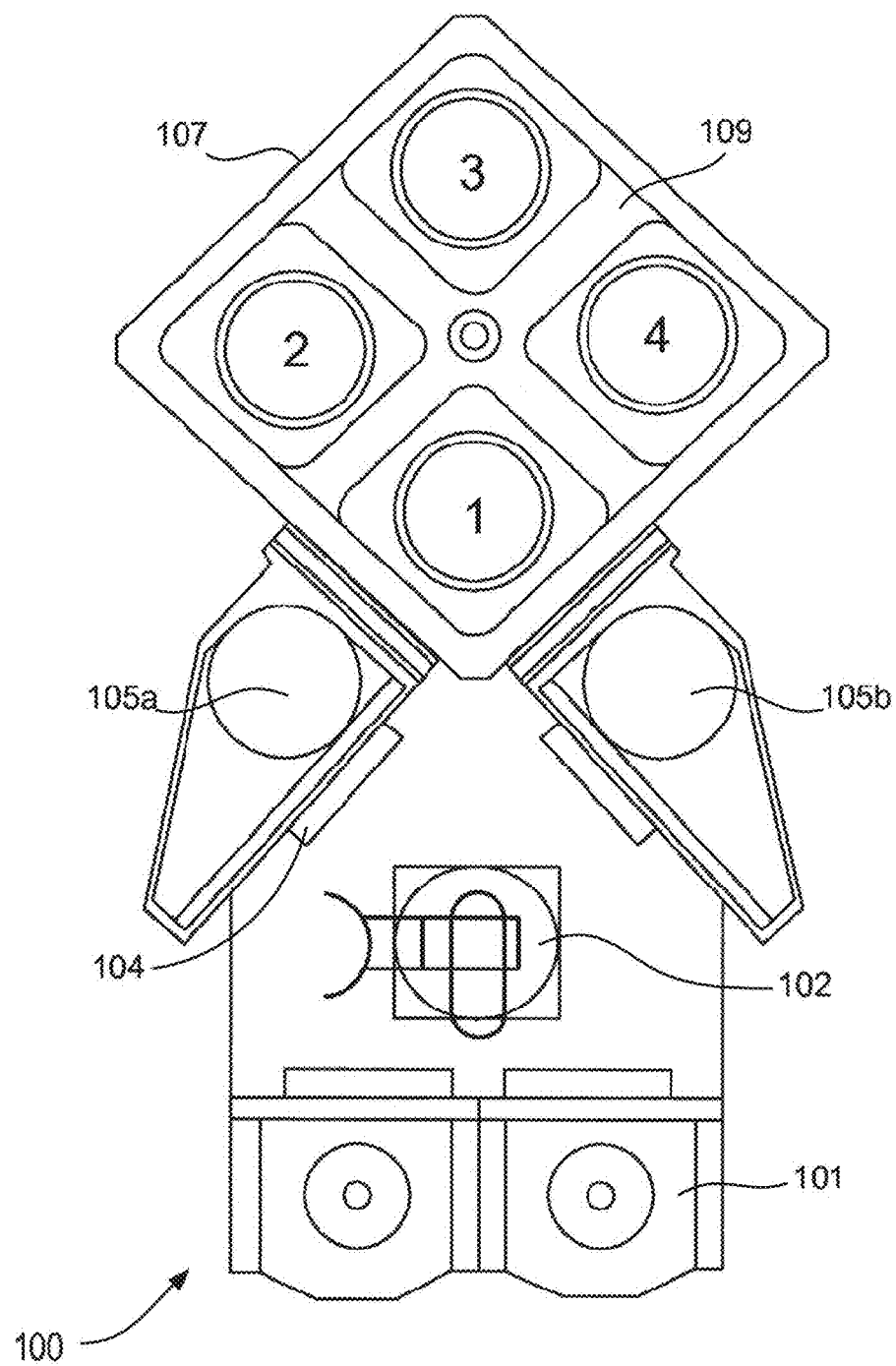
FIG. 1 shows a schematic of a multi-station processing tool that is configured to perform UV curing.

FIG. 1 shows a schematic of a multi-station processing tool that is configured to perform UV curing as disclosed in commonly-assigned U.S. Pat. No. 9,073,100, the disclosure of which is hereby incorporated by reference. The wafer enters the system 100 from a cassette loaded through a pod 101, such as the front opening unified pod (FOUP) used in 300 mm wafer systems. A robot 102, at atmospheric pressure, moves the wafer from the cassette to one of two load locks 105a or 105b. For example, the wafer enters the loadlock 105a through an atmospheric port 104 and is placed on a loadlock pedestal. The atmospheric port 104 to the atmospheric environment then closes; and the loadlock 105a is pumped down, to the same pressure or slightly above the pressure in the reactor 107. At the same time, the wafer is centered and aligned and may be heated in the loadlock on the pedestal. Then a transfer port to a reactor 107, maintained at a low pressure less than that of an atmosphere, such as a vacuum, opens, and another robot places the wafer into the reactor on a pedestal of a first station in the reactor. The above example used load lock 105a for ingress of the wafer, but load lock 105b may be used also.

The reactor 107 in the depicted wafer processing tool has four stations, numbered from 1 to 4. Each station is capable of performing ultraviolet radiation treatment simultaneously with the other stations. The wafer is indexed through the reactor stations using wafer indexing mechanism 109, which may include carrier rings and a spindle. At the end of processing at each station, the wafer is indexed to the next station for further processing. At the end of processing, the wafer is returned to station 1. The wafer then leaves the reactor through a transfer port to a loadlock 105a or 105b, where the wafer is cooled on the cooling pedestal before finally returning to the cassette in the pod 101. Because there are two loadlocks 105a and 105b, either one can be used for egress or ingress to the reactor, or both. In this particular wafer processing tool configuration, the only wafer access to the reactor 107 is through station 1, though in other configurations the loadlocks may access different stations.

The stations in the multistation chamber shown in FIG. 1 share a same vacuum environment. Other configurations with single station chambers or chambers having more or fewer stations are possible.

Figure 2:
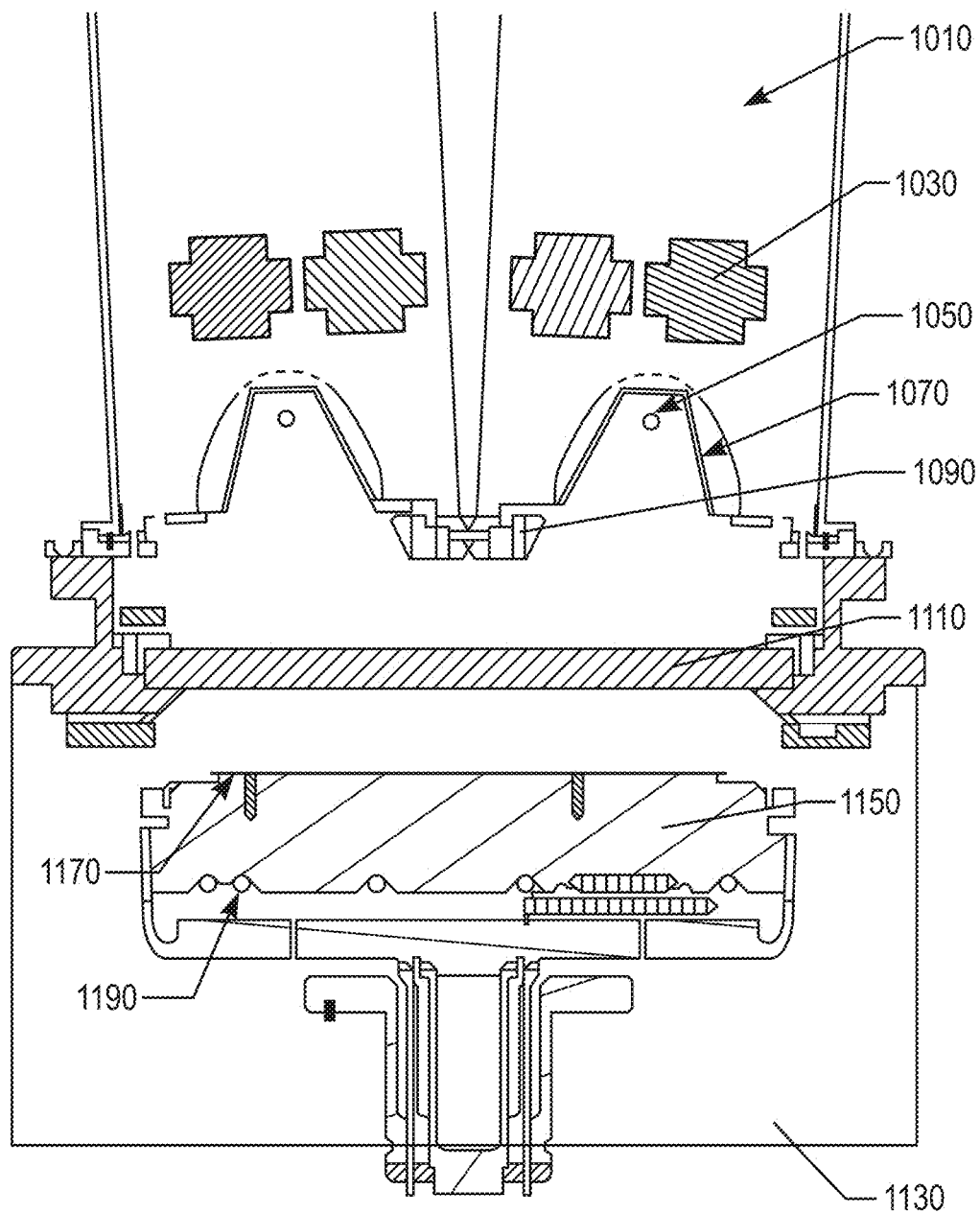
FIG. 2 is a cross-section schematic diagram of a semiconductor processing chamber.

FIG. 2 is a schematic representation of a semiconductor processing chamber with a UV radiation source, as described in U.S. Published Patent Application 2016/0258057, the disclosure of which is hereby incorporated by reference. In FIG. 2, UV lamp assemblies 1010 are mounted on top of process chamber 1130. Each lamp assembly 1010 includes transformers 1030 and magnetrons (not shown) that pump microwave energy into the lamp, UV bulb 1050, and reflectors 1070. As shown, UV detector assembly 1090 is mounted between two lamp assemblies 1010. A UV transmissive window 1110 may transmit UV radiation from the bulbs 1050 to a substrate 1170 below in the chamber. The substrate 1170 sits on a substrate holder 1150, that may be heated, cooled or both. As shown, a heater coil 1190 is embedded in the substrate support 1150. The UV lamp assembly 1010 can be replaced by a lamp assembly with torus shaped UV bulb as described below. In some implementations, the process chamber may be a part of a multi-station semiconductor processing system and each process chamber may include a substrate holder, one or more chamber windows, and one or more UV lamp assemblies.

For UV curing especially semiconductor related applications, high deep UV and sub-200 nm radiations are desired. Although high power, high pressure mercury (Hg) bulbs are available for UV curing, the high Hg pressure (typically >1000 Torr) leads to insufficient emissions below 200 nm. While low pressure Hg and amalgam bulbs have efficient emissions at 254 nm and 185 nm, the power is too low for applications demanding high deep UV output. It has been discovered that high power, low pressure (<100 Torr) lamps, such as the one described in U.S. Pat. No. 7,569,791, have short UV bulb life (typically <100 hours) which prevents high power, low pressure Hg lamps being economical for use in semiconductor related applications and other applications. As described below, the UV bulb lifetime issue associated with high power, low pressure Hg lamps is solved by providing an atomic layer deposition (ALD) coating on an inner surface of the UV bulb.

In order to improve the UV bulb's lifetime of the high power low pressure UV lamp, a plasma resistance coating has been developed and its thickness has been optimized with the use of atomic layer deposition (ALD) technology—this coating solved a long unresolved bulb fast degradation (<100 hour bulb life time) issue associated with high power, low pressure Hg lamp operation. ALD technology can provide a conformal pinhole free coating to protect the internal surface of the UV bulb from Hg plasma penetration during high power (>10 W/cm$^2$ loading) operation, the strong film adhesion produced by ALD technology also allows for coatings to survive high bulb operation temperature (~800° C.). The ALD coating is preferably of alumina material to provide adequate plasma resistance and also provide low DUV absorption which allows higher UV output. Coating thickness is preferably thick enough to provide plasma protection but not too thick to suffer from cracking/peeling issues due to thermal expansion. A preferred thickness of an ALD alumina coating is about 100 nm to about 200 nm, more preferably about 140 nm to about 160 nm, with 140 nm being a most preferred thickness for optimum transmissions of main Hg emission lines (254 nm and 185 nm).

A high power low pressure Hg lamp is very favorable for UV curing applications due to its enhanced DUV emission spectrum and high output power. However, there is an unmet need for an improved Hg bulb which provides a longer lifetime to minimize disruption to semiconductor manufacturing operations and avoid the high cost of bulb replacement.

Low power low pressure Hg lamps, such as fluorescent lamps and amalgam lamps, often have a rare earth element coating on the bulb's internal surface to protect the glass from Hg plasma interaction. Those coatings are typically dip coated in an aqueous solution; multiple coating layers are sometime used to gradually match the thermal expansion and to compensate for the expected film imperfection. While such applied coatings have successfully extended bulb lifetime for low power low pressure Hg lamp operations (power loading <0.5 W/cm$^2$, temperature <200° C.), such coatings are not suitable for high power low pressure bulb operation. Moreover, because it is difficult to achieve desired thicknesses with dip coatings, it is difficult to optimize UV transmission. Thus, there is a need for a robust bulb coating which can withstand high power plasma attack as well as survive high temperature operation to enable bulbs to have at least thousands hour service lifetime during high power low pressure lamp operation.

In an embodiment, an ultraviolet (UV) bulb includes a plasma resistant coating using atomic layer deposition (ALD) technology. The coating produced by the atomic layer deposition technology, once optimized to desired thickness such as about 100 nm to about 200 nm, preferably about 120 nm to about 160 nm, and most preferably about 140 nm, can withstand high temperature bulb operation and provide the glass protection at the same time. A preferred coating is alumina to take advantage of its low DUV absorption for highest possible UV outputs. ALD technology also allows for coating thickness to be precisely controlled to optimize transmission of the main Hg emission lines (185 nm/254 nm).

Use of ALD technology to coat an inner surface of an ultraviolet bulb can provide Hg plasma damage protection. The ALD plasma resistant coating preferable has a thickness suitable for providing a long service bulb lifetime during high power low pressure Hg lamp operation. Unlike dip coatings, ALD technology can provide a conformable pinhole free coating as well as a strong bond between the film and the glass which makes it possible to survive high temperature operations. In addition, the ALD coating process can deposit a low UV absorption material such as alumina for maximized UV outputs. Coatings thickness can be controlled precisely with the ALD process to optimize the DUV transmission as well. Comparing a UV bulb without a plasma resistant coating to a bulb with an ALD coating, lifetime of a high power low pressure Hg bulb operation can be increased from <100 hours to over thousands of hours.

Figure 3:
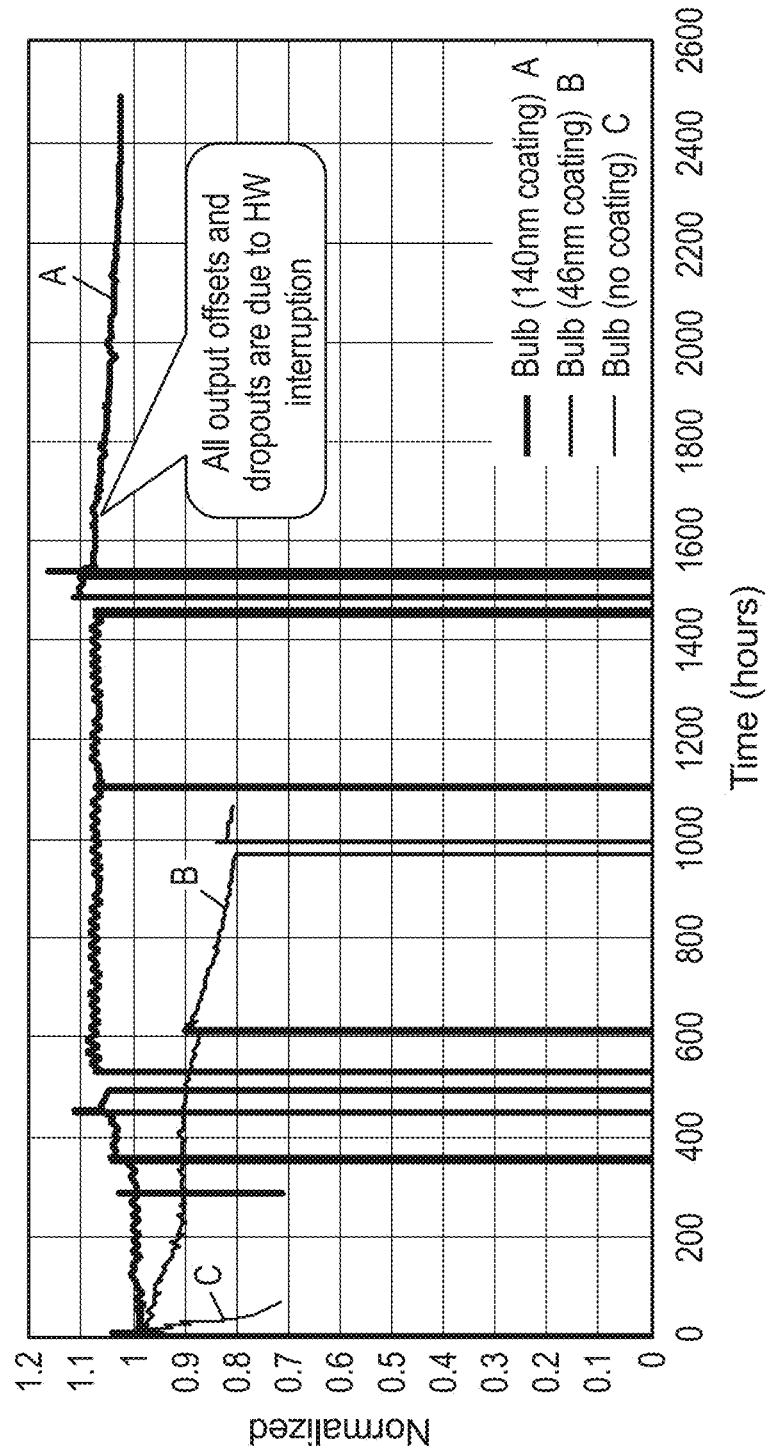
FIG. 3 is a graph which shows the output stability of low pressure Hg bulbs with and without a protective ALD coating tested under high power (14~15 W/cm$^2$).

FIG. 3 is a graph which shows the output stability of Hg bulbs with and without a protective ALD coating tested under high power (14~15 W/cm$^2$) conditions. A UV bulb without a coating degraded rapidly (typically ~30% degradation within 100 hours as shown by curve C). A UV bulb with a thin ALD coating (46 nm thick ALD alumina coating as shown by curve B) extended the life time dramatically, but the degradation is still too high (~20% at ~1000 hours) to be useful. A UV bulb with an optimized coating (~140 nm thick ALD alumina coating as shown by curve A) has demonstrated very low degradation (~10% over ~2400 hours) which makes it attractive for commercial use.

FIGS. 4A-C show the status of three UV bulbs as a function of time under the same high power (14~15 W/cm$^2$) conditions. In FIG. 4A, the dark patches were formed on the envelope of a UV bulb without a plasma resistant coating after <100 hours of operation. In FIG. 4B, a UV bulb with a thin (46 nm thick) ALD alumina coating shows striation patterns after ~1000 hours of operation. FIG. 4C shows a UV bulb with a thicker ALD alumina coating (~140 nm thick) and the UV bulb had no dark patterns formed after more hours of operation than the UV bulbs shown in FIGS. 4A and 4B. The UV bulb shown in FIG. 4C had a clear envelope even after ~2400 hours of operation.

Figure 5:
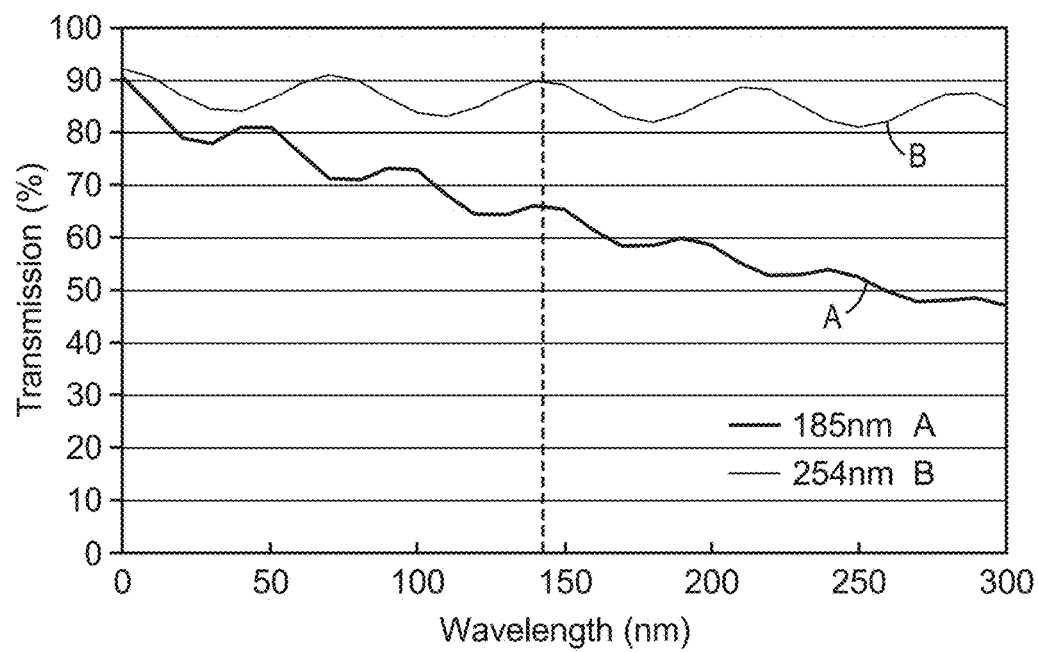
FIG. 5 shows the UV transmission versus coating thickness for the two main Hg emission lines (185 nm/254 nm).

The graph shown in FIG. 5 shows the UV transmission versus coating thickness for the two main Hg emission lines (185 nm/254 nm). The optimized coating thickness of ~140 nm has proven to provide the best UV bulb glass protection. This thickness, which is the 2nd peak transmission of the 254 nm emission (curve B) and the 3rd peak transmission of the 185 nm emission (curve A), also yields the optimized overall UV transmission.

The ALD aluminum oxide coating can be formed by subjecting the interior of a glass tube suitable for use as a mercury bulb of an ultraviolet lamp to repetitive cycles of flowing an aluminum source gas, a purge gas, an oxygen source gas and a second purge gas while maintaining the glass tube at a suitable temperature. For example, the aluminum source gas can be trimethyl aluminum (TMA) supplied for a suitable time such as 0.1 to 3 seconds, the purge gas can be nitrogen supplied for a suitable time such as 0.1 to 3 seconds, the oxygen source can be oxygen or water vapor supplied for a suitable time such as 0.1 to 3 seconds, and the second purge gas can be nitrogen supplied for a suitable time such as 0.1 to 2 seconds. The cycles are repeated until the ALD aluminum oxide coating reaches a desired thickness. For example, assuming a film thickness of about 1 Å forms in each cycle, at least 1000 cycles will be needed to obtain a film thickness of 100 nm or more. Unlike a sintered film composed of alumina particles, the ALD alumina is a conformal pinhole free film which is free of alumina particles and is the only layer of material inside the glass tube. That is, unlike fluorescent bulbs which contain a luminescent material such as a phosphor layer, the ultraviolet lamp disclosed herein is a low pressure electrodeless UV bulb which lacks a luminescent material layer inside the UV bulb.

Figure 6:
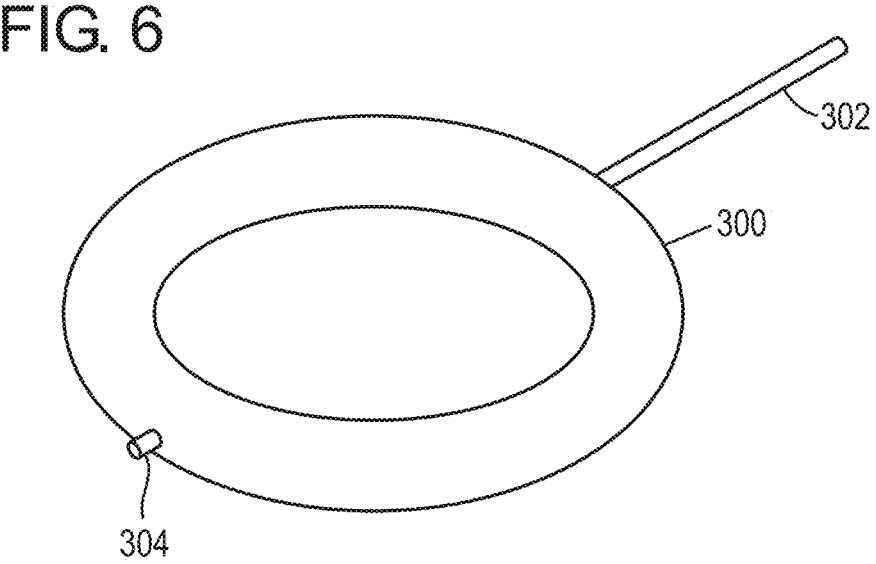
FIG. 6 shows a glass tube having inlet and outlet ports for manufacturing an ultraviolet bulb having an ALD alumina layer according to a preferred embodiment.

FIG. 6 shows a glass tube 300 suitable for manufacturing an envelope of a UV lamp wherein a long tube 302 is used for an inlet of deposition gases and a short tube 304 is used as an outlet for the deposition gases and byproducts during an internal ALD surface coating process. The ALD coating is deposited on the inner (internal) surface of the tube by repeating a sequence of steps until the desired film thickness is achieved. In depositing an aluminum oxide (alumina) coating by atomic layer deposition, an aluminum containing precursor such as trimethylaluminum (Al(CH$_3$)$_3$ or TMA) is introduced into the tube, the tube is purged, an oxygen reactant such as water vapor, ozone or oxygen radicals is introduced into the tube to provide a monolayer of aluminum oxide, the tube is purged and the cycle repeated until the layer of aluminum oxide has a desired thickness. The ALD alumina coating is in direct contact with the inner surface of the tube and preferably consists entirely of aluminum oxide, i.e., the tube does not contain any other material (such as dopants, phosphors, other layers) on the inner surface. The ALD alumina coating is preferably a conformal pinhole free film which does not contain particles of any other material, i.e., the ALD coating is the only layer of material on the inner surface of the tube. After the ALD coating has been built up to a desired thickness, the short tube is pinched off by melting and sealing the glass. The long tube is then used for bulb emission material filling (mercury and inert gas) after which it is pinched off by melting and sealing the glass.

The UV bulb can be used for curing a film on a semiconductor substrate by supporting a semiconductor substrate in a curing chamber; and exposing a layer on the semiconductor substrate to UV radiation produced by the UV bulb. For example, the layer can be a dielectric layer and the UV radiation can remove porogens from the dielectric layer. Details of equipment and method steps for carrying out curing of films on semiconductor substrates can be found in commonly-assigned U.S. Published Patent Application 2016/0138160, the disclosure of which is hereby incorporated by reference. The UV radiation also promotes cross-linking within the material. In another method, the UV bulb can be used to generate ozone for cleaning the semiconductor substrate. For example, oxygen gas (O$_2$) can be flowed into the semiconductor processing chamber at a suitable flow rate and for a suitable time while the pressure is maintained in a range of about from 200 Torr to 800 Torr, and the O$_2$ gas can be converted to ozone by turning on the UV bulb to provide UV energy.

The UV bulb is preferably electrodeless and is energized by electromagnetic radiation which sustains a plasma from a gas mixture enclosed in the UV bulb. For example, the UV bulb can also be used for heating and curing materials such as, adhesives, inks and coatings. Other uses include UV disinfection and sterilization of liquids, gases, articles such as containers, and spaces such as rooms or defined environments. For treating gases or liquids, the UV bulb can be mounted in an in-line reactor in which gases and liquids are exposed to UV radiation produced by the UV bulb. For example, a fluid or object can be sterilized by energizing the UV bulb and exposing UV radiation produced by the UV bulb to a fluid or object for a duration of time sufficient to provide effective sterilization of microorganisms within the fluid or effective sterilization of microorganisms on a surface of the object. In an embodiment, the UV bulb can be used for generation of ozone by exposing air or oxygen to UV radiation produced by the UV bulb and the ozone can be used to disinfect or sterilize liquids, gases, objects such as containers or spaces such as rooms. The ozone generated by the UV bulb can also be useful in reducing odors by disinfecting and sanitizing objects, gases, liquids and open areas. A preferred UV bulb is an electrodeless UV bulb and the ionizable medium in the electrodeless bulb can be energized into a plasma state by one or more magnetic cores which generate a toroidal plasma in the UV bulb. Details of a suitable power system comprising an electromagnetic radiation source for inducing electric current inside a tubular shaped UV bulb can be found in U.S. Pat. No. 7,569,791, the disclosure of which is hereby incorporated by reference.

As used herein, the term "about" when used in connection with numerical values means plus or minus 10%.

While this invention has been described in terms of several embodiments, there are alterations, modifications, permutations, and substitute equivalents, which fall within the scope of this invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention. The use of the singular in the claims does not mean "only one," but rather "one or more," unless otherwise stated in the claims.

What is claimed is:

1. An envelope of an ultraviolet (UV) bulb, the envelope comprising:
    a tube of UV transmissive material configured to contain a UV emissive material; and
    a plasma resistant coating on an inner surface of the tube wherein the coating has been deposited by atomic layer deposition (ALD) and is the only material attached to the inner surface of the tube, wherein the coating consists of aluminum oxide.

2. The envelope of claim 1, wherein the tube is an endless tube having a circular shape.

3. The envelope of claim 1, wherein the UV transmissive material comprises quartz or fused silica.

4. The envelope of claim 1, wherein the tube has a wall thickness of about 1 to about 2 mm.

5. The envelope of claim 1, wherein the coating has a thickness of at least 100 nm and no greater than about 200 nm.

6. The envelope of claim 1, wherein the coating has a thickness of about 120 to 160 nm.

7. The envelope of claim 2, wherein the endless tube has an outer torus diameter of about 200 mm and the tube has an outer diameter of about 30 mm.

8. The envelope of claim 3, wherein the ALD aluminum oxide coating is a pinhole free conformal coating.

9. A UV bulb comprising the envelope of claim 1, wherein the envelope contains a UV emissive material and lacks a luminescent material inside the UV bulb.

10. The UV bulb of claim 9, wherein the UV emissive material comprises mercury.

11. The UV bulb of claim 9, wherein the tube is hermetically sealed and includes an inert gas.

12. The UV bulb of claim 9, wherein the UV bulb is electrodeless and pressure inside the bulb is below 100 Torr.

13. The UV bulb of claim 9, wherein tube has an outer diameter of about 30 mm and the tube is an endless tube having a circular shape with an outer torus diameter of about 200 mm.

14. A UV lamp assembly including the UV bulb of claim 9.

15. A method of processing a semiconductor substrate, comprising supporting a semiconductor substrate in a processing chamber; and exposing the semiconductor substrate to UV radiation produced by the UV bulb of claim 9.

16. The method of claim 15, wherein the semiconductor substrate includes one or more dielectric layers and the UV radiation removes porogens from the one or more dielectric layers, increases strength of the one or more dielectric layers and/or repairs damage to the one or more dielectric layers.

17. A method of processing a semiconductor substrate, comprising supporting a semiconductor substrate in a processing chamber; generating ozone by exposing oxygen to UV radiation produced by the UV bulb of claim 9, and cleaning the semiconductor substrate surface with the ozone.

18. A method of sterilizing a fluid or object, comprising:
    energizing the UV bulb of claim 9 and exposing UV radiation produced by the UV bulb to a fluid or object for a duration of time sufficient to provide effective sterilization of microorganisms within the fluid or effective sterilization of microorganisms on a surface of the object.

* * * * *